United States Patent
Klocek et al.

(10) Patent No.: US 11,120,898 B1
(45) Date of Patent: Sep. 14, 2021

(54) FLEXIBLE ENCOUNTER TRACKING SYSTEMS AND METHODS

(71) Applicant: Allscripts Software, LLC, Raleigh, NC (US)

(72) Inventors: Stefan Mills Klocek, Berkeley, CA (US); Richard Loomis, Alameda, CA (US); Gerald Gordinier, II, San Francisco, CA (US); Jonathan Board, San Francisco, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 214 days.

(21) Appl. No.: 16/538,705

(22) Filed: Aug. 12, 2019

Related U.S. Application Data

(63) Continuation of application No. 14/697,098, filed on Apr. 27, 2015, now Pat. No. 10,381,113.

(51) Int. Cl.
*G16H 10/60* (2018.01)
*G16H 30/20* (2018.01)

(52) U.S. Cl.
CPC ............ *G16H 10/60* (2018.01); *G16H 30/20* (2018.01)

(58) Field of Classification Search
CPC .............................. G16H 10/60; G16H 30/20
USPC ............................................................. 705/3
See application file for complete search history.

(56) References Cited

U.S. PATENT DOCUMENTS

| | | | | |
|---|---|---|---|---|
| 8,311,848 B2* | 11/2012 | Subash | ................. | G16H 10/60 705/2 |
| 8,380,533 B2* | 2/2013 | Reicher | ............... | G06F 21/6245 705/2 |
| 2002/0035487 A1* | 3/2002 | Brummel | ............... | G16H 70/20 705/3 |
| 2011/0202370 A1* | 8/2011 | Green, III | ............. | G16H 10/20 705/3 |
| 2012/0109686 A1* | 5/2012 | Higbie | ................. | G16H 10/60 705/3 |
| 2016/0314248 A1 | 10/2016 | Klocek et al. | | |

OTHER PUBLICATIONS

U.S. Appl. No. 14/455,091, Douglass et al., "Electronic Health Records Data Management Systems and Methods," filed Aug. 8, 2014.

(Continued)

*Primary Examiner* — Michael Tomaszewski
(74) *Attorney, Agent, or Firm* — Medley, Behrens & Lewis, LLC

(57) ABSTRACT

Embodiments include a customizable encounter document whose contents are populated based on a template for the current patient, a template for all the user's patients, or a combination of templates. The contents include data modules retrieved from various databases and are arranged according to the user's work flow. The contents are presented in one view, a scrollable pane, to assist the user when making medical decisions. The user can make changes to the contents on the scrollable pane in real time that may affect one or more of the templates. Once the customizable encounter document is signed, the contents are captured, de-identified, and saved, along with a link of the captured contents with the user, and/or the patient's EHR.

20 Claims, 9 Drawing Sheets

(56) References Cited

OTHER PUBLICATIONS

U.S. Appl. No. 14/318,492, Matthew Christopher Douglass, "Medical Professional Application Integration Into Electronic Health Record System," filed Jun. 27, 2014.
"Non-Final Office Action for U.S. Appl. No. 14/697,098", dated Dec. 27, 2017, 11 pages.
"Response to the Non-Final Office Action for U.S. Appl. No. 14/697,098", filed Jun. 27, 2018, 28 pages.
"Final Office Action for U.S. Appl. No. 14/697,098", dated Aug. 10, 2018, 18 pages.
"Notice of Appeal for U.S. Appl. No. 14/697,098", filed Sep. 25, 2018, 2 pages.
"Appeal Brief for U.S. Appl. No. 14/697,098", filed Dec. 21, 2018, 37 pages.
"Notice of Allowance and Fees Due for U.S. Appl. No. 14/697,098", dated Mar. 27, 2019, 8 pages.

\* cited by examiner

300

Help | Feedback | Logoff     David Faraday | Mt Hellen's Health Clinic

Patients Sarah Williams x     Terrance Jones x     Ed Lee x     Levi Swanson x Sarah Williams   30 Female   2/5/1984   Blueshield   415.925.1230   Saved at 9:00PM

| Summary | Timeline | Profile | 03/15/14 x | Actions ∨ |

Office visit ∨ | Show ... + | Search 🔍 ❓ | Save | Sign

Encounter details ～325                                                                                                      320

- Today, 03/15/14   Office visit   Seen by Jonathan Jones NP   John Cardis, John's Hospital for Children   Unsigned

Chief complaint  Record
― 330

Migranes
― 335

Vitals   Show metric   Show growth charts

| HEIGHT | WEIGHT | BMI | TEMP | BP | PULSE | RR | 02 SAT | PAIN |
| 69 in | 142 lbs | 29.2 | 98.8°F oral | 169/77 | 71 | 61 | 99% RA | 0 |

― 340

Problem list   Record

- Sciatica   721.3   Started today, 03/15/14   Updated 03/15/14   Jose Gonzales, NP
- Obesity, unspecified   278.00   Started 03/12/14
- Unspecified essential hypertension   278.00   Acute   Started 02/12/14
- Show historical (4)

From PMH: Back pain
― 350

Allergies   Record

Drug allergies ～ 353

- Penicillin   Severe   Anaphylactic shock ～ 355

Show inactive (4)

Show food and environmental allergies (4)

From PMH: Amoxicillin
― 360

Medications   Record   Order   Sort by start date ∨   Show ∨

- naproxen 500mg oral tablet   2x a day   Started 02/24/13
- lisinopril 500mg oral tablet   Take two times a day with breakfast, once after lunch. Continue for two months. Take with food. Do not drink with med.   Started 02/14/13
- acemethipine   Started 02/24/13
- naproxen 500mg oral tablet   2x a day   started 02/04/13
- lisinopril 500mg oral tablet   Take two times a day with breakfast, once after lunch. Continue for two months. Take with food. Do not drink with med.   Started 01/24/13

Help | Feedback | Logoff  David Faraday | Mt Hellen's Health Clinic

Patients Sarah Williams x    Terrance Jones x    Ed Lee x    Levi Swanson x

Sarah Williams  30 Female  2/5/1984  Blueshield  415.925.1230  Saved at 9:00PM

| Summary | Timeline | Profile | 👤 03/15/14 x |    Actions ⌄

| Office visit ⌄ | Show ... | + | Search 🔍 | ❔ |    Save    Sign

Sidebar: Home, Schedule, Tasks, Charts, Messages, Reports, Settings, Help, Feedback, Lock ~405
Allergies   Record   Show ⌄   ~410

- Record an allergy

Drug allergies  ~415

- Penicillin  Severe
  Show inactive (4)

Show food and environmental allergies (4)

From PMH: Amoxicillin
~460
Medications   Record   Order   Sort by start date ⌄   Show ⌄

- naproxen 500mg oral tablet    2x a day    Started 02/24/13
- lisinopril 500mg oral tablet    Take two times a day with breakfast, once after lunch. Continue for two months. Take with food. Do not drink with med.   Started 02/14/13
- naproxen 500mg oral tablet    2x a day    started 02/04/13
- lisinopril 500mg oral tablet    Take two times a day with breakfast, once after lunch. Continue for two months. Take with food. Do not drink with med.   Started 01/24/13
- naproxen 500mg oral tablet    2x a day    started 01/24/13
- lisinopril 500mg oral tablet    Take two times a day with breakfast, once after lunch. Continue for two months. Take with food. Do not drink with med.   Started 01/24/13
- another specific product dosemg route    Started 02/24/13

Show all active (28)
Show historical (5)
From PMH: Naproxin
~470
Family health history   Record ⌄

- Aids   Parent - Father
- Cancer   Parent - Father
- Degenerative neoplasitic disease   Parent – Father, Parent – Mother, Cousin (Judy)
- Exema   Sibling (Justine)
- Face disorder   Sibling - Brother
- Glycoccemic cancer   Other relative (step-brother)
- Hypertension   Unknown relative

Right panel (420):

Allergies   ~430
Record allergy

| Drug | Food | Environmental |

Type if search for drug allergies   🔍

440

Done   Next

Help | Feedback | Logoff    David Faraday | Mt Hellen's Health Clinic

Patients Sarah Williams x    Terrance Jones x    Ed Lee x    Levi Swanson x

630

Sarah Williams  30 Female  2/5/1984  Blueshield  415.925.1230  Saved at 9:00PM Home

| Summary | Timeline | Profile | 👤 03/15/14 x |  Actions ⌄

Schedule

Office visit ⌄ | Show ... + | Search 🔍 ❓ | Save | Sign ← 710

Tasks

Encounter details

Sign this encounter

This will permanently finalize this encounter as a legal document. You will not be able to make edits after signing.

Cancel | Sign

- Today, 03/15/14  Office visit  Seen by Jonathan Jones NP  John Cardis, Jo[...]

Charts

Chief complaint

Migranes

Messages

Vitals  Show metric  Show growth charts

| HEIGHT | WEIGHT | BMI | TEMP | BP | PULSE | RR | 02 SAT | PAIN |
| --- | --- | --- | --- | --- | --- | --- | --- | --- |
| 69 in | 142 lbs | 29.2 | 98.8°F oral | 169/77 | 71 | 61 | 99% RA | 0 |

Reports

Problem list

Settings

- Sciatica  721.3  Started today, 03/15/14  Updated 03/15/14  Jose Gonzales, NP
- Obesity, unspecified  278.00  Started 03/12/14
- Unspecified essential hypertension  278.00  Acute  Started 02/12/14
- Show historical (4)

Help

From PMH: Back pain

Allergies  Record

Feedback

Drug allergies

- Penicillin  Severe
  Show inactive (4)

Lock

Show food and environmental allergies (4)

From PMH: Amoxicillin

Medications  Record  Order  Sort by start date ⌄  Show ⌄

- naproxen 500mg oral tablet  2x a day  Started 02/24/13
- lisinopril 500mg oral tablet  Take two times a day with breakfast, once after lunch. Continue for two months. Take with food.
  Do not drink with med.  Started 02/14/13
- naproxen 500mg oral tablet  2x a day  started 02/04/13
- lisinopril 500mg oral tablet  Take two times a day with breakfast, once after lunch. Continue for two months. Take with food.
  Do not drink with med.  Started 01/24/13
- naproxen 500mg oral tablet  2x a day  started 01/24/13
- lisinopril 500mg oral tablet  Take two times a day with breakfast, once after lunch. Continue for two months. Take with
  food. Do not drink with med.  Started 01/24/13
- another specific product dosemg route  Started 02/24/13

FLEXIBLE ENCOUNTER TRACKING SYSTEMS AND METHODS

RELATED APPLICATIONS

This application is a continuation of U.S. patent application Ser. No. 14/697,098, filed on Apr. 27, 2015, and entitled "FLEXIBLE ENCOUNTER TRACKING SYSTEMS AND METHODS", the entirety of which is incorporated herein by reference.

BACKGROUND

Field

This field is generally related to documenting a patient interaction in an electronic health record.

Background

Electronic Health Records

Medical records related to a patient's health information are essential to the practice of medical care. Traditionally, medical records were paper-based documents. The emergence of electronic medical records (EMRs), which are a digital version of the paper chart that contains all of a patient's medical history from one medical practice, offers medical professionals and patients with new functionalities and efficiencies that paper-based medical records cannot provide. An EMR, which can be incorporated into an electronic health record (EHR), is a collection of electronically stored information about an individual patient's medical history. EHRs may contain a broad range of data, including demographics, medical history, medication history, allergies, immunization records, laboratory test results, radiology images, vital signs, personal statistics like age and weight, and billing information. Many commercial EHR systems combine data from a number of health care services and providers, such as clinical care facilities, laboratories, radiology centers, and pharmacies.

EHRs are a drastic improvement over paper-based medical records. Paper-based medical records require a large amount of physical storage space. Paper records are often stored in different locations, and different medical professionals may each have different and incomplete records about the same patient. Obtaining paper records from multiple locations for review by a health care provider can be time consuming, complicated, and sometimes impossible. In contrast, EHR data are stored in digital format, and thus are more secure and can be accessed from anywhere. EHR systems significantly simplify the reviewing process for health care providers. Because records in EHRs can be linked together, EHRs vastly improve the accessibility of health records and the coordination of medical care.

EHRs also decrease the risk of misreading errors by health care professionals. Poor legibility is often associated with handwritten, paper medical records, which can lead to medical errors. EHRs, on the other hand, are inherently legible given that they are typically stored in typeface. In addition, electronic medical records enhance the standardization of forms, terminology and abbreviations, and data input, which help ensure reliability of medical records, and standardization of codesets and storage of EHR data means that data from different technical information systems can be displayed in a single, unified record. Further, EHRs can be transferred electronically, thus reducing delays and errors in recording prescriptions or communicating laboratory test results.

The benefits of digitizing health records are substantial. Health care providers with EHR systems have reported better outcomes, fewer complications, lower costs, and fewer malpractice claim payments. But despite EHRs' potential in drastically improving the quality of medical care, only a low percentage of health care providers use EHR systems. While the advantages of EHRs are significant, they also carry concerns, including high costs, lost productivity during EHR implementation or computer downtime, and lack of EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as health information doctors and nurses input, documented conversations between a doctor and a patient, and information use to process or facilitate medical billing claims and documents. The HIPAA Security Rule, effective on Apr. 20, 2005 for most covered entities, adds additional constraints to electronic data security and the storage and transmission of PHI.

The high cost of EHRs also significantly hinders EHR adoption. A large number of physicians without EHRs have referred to initial capital costs as a barrier to adopting EHR systems. Cost concerns are even more severe in smaller health care settings, because current EHR systems are more likely to provide cost savings for large integrated institutions than for small physician offices. During the EHR technology's setup and implementation process, productivity loss can further offset efficiency gains. The need to increase the size of information technology staff to maintain the system adds even more costs to EHR usages.

Usability is another major factor that holds back adoption of EHRs. It is particularly challenging to develop user-friendly EHR systems. There is a wide range of data that needs to be integrated and connected. Complex information and analysis needs vary from setting to setting, among health care provider groups, and from function to function within a health care provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHRs in revolutionizing the health care system, calls for better EHR systems that are secure, cost-effective, efficient, and user-friendly.

Comprehensive EHR systems can provide capabilities far beyond simply storing patients' medical records. Because EHR systems offer health care providers and their workforce members the ability to securely store and utilize structured health information, EHR systems can have a profound impact on the quality of the health care system. In *Framework for Strategic Action on Health Information Technology*, published on Jul. 21, 2004, the Department of Health & Human Services (HHS) outlined many purposes for EHR services. The outlined purposes include, among other things, improving health care outcomes and reducing costs, reducing recordkeeping and duplication burdens, improving resource utilization, care coordination, active quality and health status monitoring, reducing treatment variability, and promoting patients' engagement in and ownership over their own health care.

Recent legislation has set goals and committed significant resources for health information technology (HIT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for health care providers to adopt and meaningfully use EHRs in their practices. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

Cumbersome Data Access, Data Arrangement, and Loss of Historical Data

The conventional access of interfaces in a patient's electronic medical chart as well as the organization of data within an interface can sometimes make a healthcare provider's practice difficult, because the interfaces do not align with the healthcare provider's work flow. During an interaction with a patient, a user of an EHR system (e.g., the healthcare provider such as a physician or a nurse) typically accesses many separate interface presentations or pages of data in the patient's EHR before making and documenting medical decisions and treatments in a separate note interface. It can be cumbersome and difficult for the user to flip back and forth to find the data they need.

Further, only data that the user enters in the note interface is saved when the note is electronically signed. Later, when a user returns to the patient's EHR, the user may not remember what data was present in the separate interfaces when medical decisions and treatments were documented in the note interface. Some users copy and paste data from various interfaces into the separate note interface. This can be a time-consuming and frustrating effort. In addition, some users may create shortcuts within a note interface that links to a different interface (e.g., an Allergies interface). But, after the note interface is saved, the data linked via the shortcut on the note interface (e.g., the Allergies interface) continues to change over time. Thus, a record of the data available at the time the note is signed is lost.

BRIEF SUMMARY

Embodiments include a customizable encounter document whose contents are populated based on a template for the current patient, a template for all the user's patients, or a combination of templates. The contents are presented in one view, a scrollable pane, to assist the user when making medical decisions. The user can make changes to the contents on the scrollable pane in real time that may affect the current patient's template, the template for all the patients, or a combination of templates. Once the customizable encounter document is signed, the contents are captured, saved, and linked to the patient's electronic medical chart.

The scrollable pane is populated with data modules pulled from various databases and arranged according to the user's work flow. The user further customizes the scrollable pane in real time (e.g., during a patient interaction, the user changes the sequence of the data modules, removes/adds data modules, or nests a data module within another data module). The customization affects the current encounter document of the patient, the patient's template for the type of encounter (e.g., if the customization was for an office visit encounter, the customization affects future office visit encounter documents associated with the patient), the template for all the user's patients (e.g., the customization affects future office visit encounter documents for all of the user's patients), or a combination of templates.

When a portion of the scrollable pane contents is being adjusted, the contents not being adjusted remain present in the scrollable pane. Once a user signs the encounter document of the patient interaction, a snapshot of the data in the scrollable pane is captured and saved in the patient's EHR. Thus, the data available at the time the encounter document is signed are preserved, and viewable by the user.

Embodiments include a method, computer-readable storage, and system for documenting an encounter including retrieving an electronic health record (EHR) of a patient, receiving a request to open an encounter document associated with the patient, and populating a scrollable pane of the encounter document based on at least one of an encounter document template of the patient, an encounter document template for all patients, or a combination of templates. The populating includes accessing one or more databases. The contents of the scrollable pane comprise at least one of a data module, a subsection, or data. Embodiments also include adjusting, in real time, at least one of the data module, the subsection, or the data, where the contents not being adjusted remain present in the scrollable pane. Embodiments further include updating, based on the real-time adjusting, at least one of the encounter document template of the patient, the encounter document template for all patients, or a selected combination of templates. After a user electronically signs the encounter document, embodiments include creating a permanent snapshot of the encounter document, where the contents of the scrollable pane are not changeable, storing the permanent snapshot, and storing a link of the permanent snapshot with the user and/or the patient's electronic medical chart.

Further embodiments, features, and advantages, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable one of ordinary skill in the art to make and use the disclosure.

FIG. 3 illustrates an example interface showing an office visit encounter document, according to an embodiment.

FIG. 4 illustrates an example interface showing data being added to a subsection, according to an embodiment.

FIG. 5 illustrates an example interface showing data module choices, according to an embodiment.

FIG. 7 illustrates an example interface that allows for the creation of a snapshot, according to an embodiment.

FIG. 9 illustrates a conventional patient EHR interface.

The drawing in which an element first appears is typically indicated by the leftmost digit or digits in the corresponding reference number. In the drawings, like reference numbers may indicate identical or functionally similar elements.

DETAILED DESCRIPTION

Figure 1:
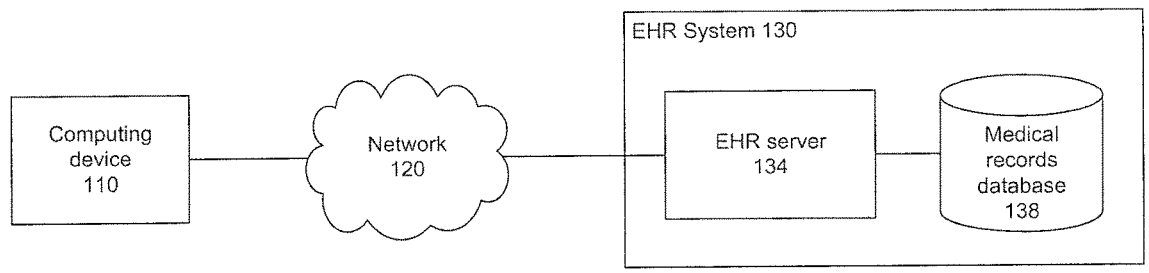
FIG. 1 is a diagram illustrating an example system for documenting an encounter, according to an embodiment.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 9:
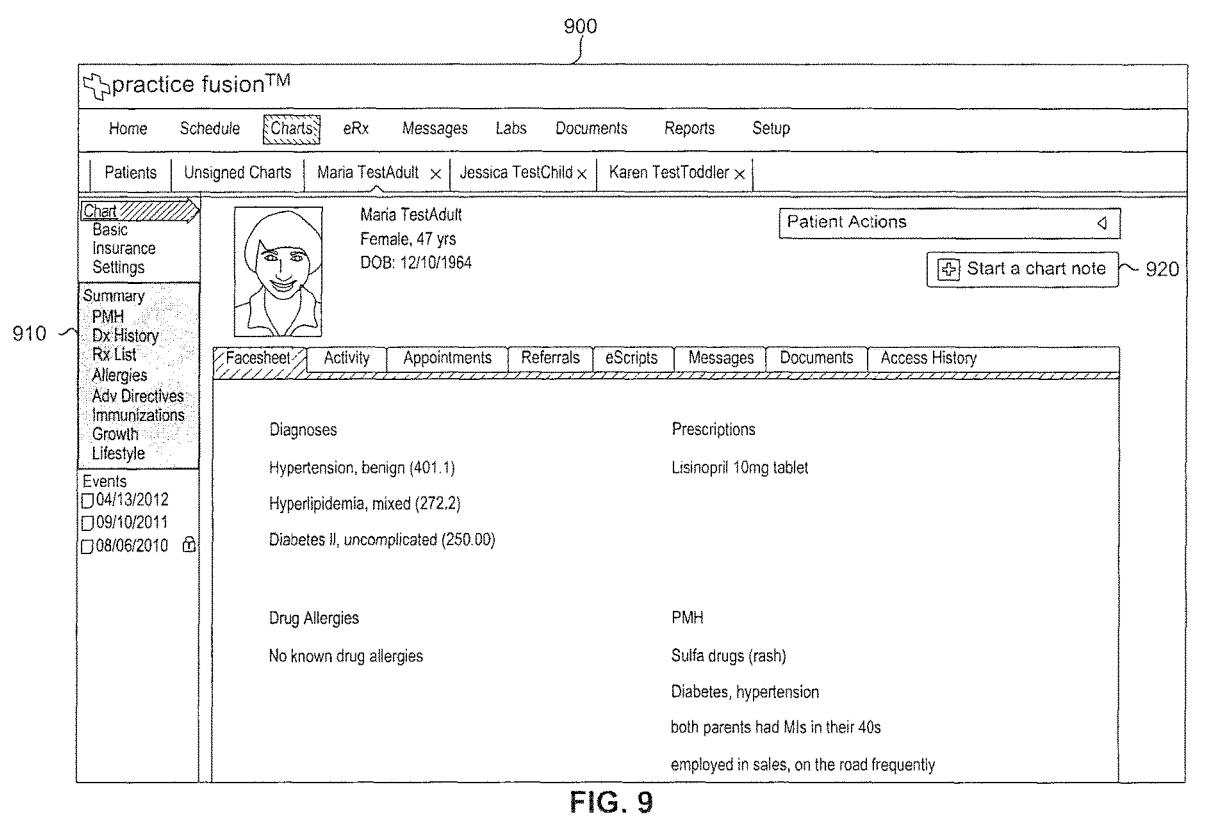

To document an interaction with a patient, an EHR system user typically accesses many separate interfaces or pages of data in the patient's electronic medical chart before making and documenting medical decisions and treatments in a separate note interface. FIG. 9 illustrates a conventional patient EHR interface 900 that presents a patient's EHR on separate interfaces. The EHR mimics a patient chart, in that the EHR contains various types of information about a particular patient, from basic facts to more detailed medical information. Disparate types of information may be separated into various tabs, as illustrated in FIG. 9. For example, FIG. 9 has a home screen for the patient that includes tabs for "messages" and "documents." There is also a "Start a chart note" button 920 that may be selected when a user, such as a healthcare provider, wishes to add new information into the record.

Summary 910 lists various, separate interfaces that form the patient's EHR. These interfaces may include, for example, past medical history (PMH), diagnosis (Dx) history, prescription (Rx) history, allergies, immunizations, and growth chart. When a user interacts with a patient, the user typically views each of these interfaces one at a time before making a medical decision. To document the decision and/or a treatment based on the interfaces of data, the user may click on "Start a chart note" button 920 to enter information into a note interface. Only data entered in the note interface is saved. Later, when a user returns to the patient's EHR, the user may not remember which data from the separate interfaces were present when the prior medical decisions and treatments were documented in the note interface.

Flexible Encounter Tracking

In embodiments, an EHR system user is a healthcare provider, such as a physician or a nurse. Each user establishes a work flow for their practice. A work flow refers to tasks and the sequence in which the tasks are completed. Work flows are different depending on a type of medical practice. For example, pediatricians perform different tasks from cardiologists, who also perform different tasks from obstetricians. And even within a type of medical practice, for example, pediatrics, users have preferences for how and when a given task is performed. In embodiments, a work flow involves one or more data modules. Example data modules include "Allergies", "Vitals", "Medications", and "Note". A data module may include subsections. For example, the Allergies data module may include subsections for food allergies and drug allergies.

A user's interaction with a patient may be called an encounter, and there are different types of encounters. Encounter types may include, but are not limited to, the following: an office visit encounter; a hospital visit encounter; a telephone encounter; and an order encounter. In an order encounter, for example, the user may write a prescription. A user records notes about a patient encounter in an encounter document.

In embodiments, a user views an encounter document presented on a single interface, a scrollable pane that includes one or more data modules. The data modules are retrieved from one or more databases, and are presented in a single view so that the user does not have to flip back and forth between different interfaces and/or tabs to view medical data. Embodiments allow a user to interact with the interface to customize an encounter document at both a template level and a data level in real time (e.g., during an encounter). A user creates a template based on his or her work flow. The template determines which data modules are retrieved from a medical records database for inclusion in the scrollable pane of an encounter document. A template may be applied for all the user's patients, a specific patient, or a subset of the user's patients. In addition, a combination templates may be selected and applied.

In addition, embodiments allow a user to dynamically customize data modules in the scrollable pane. The sequence in which the data modules are serialized in the scrollable pane during an encounter may also be customized. The customization may affect a patient's current encounter document before being signed, the patient's encounter document template, an encounter document template for all the user's patients, or a combination of templates. For example, data modules, subsections, and data may be added, removed, and/or changed within the scrollable pane. While the customization takes place, the remaining data in the scrollable pane remains present. This presence allows the user to scroll up and down to review existing data as the user makes changes. Once the user signs the encounter document, the data in the scrollable pane of the encounter document may be viewed but not changed. For example, data modules, subsections, and data in the scrollable pane of the encounter document are captured in a snapshot and become a permanent record of the data available at the time the encounter is signed. Later, when a user returns to the patient's EHR, the user may access a signed encounter document to see not only the notes that a user made during the encounter, but also the data that was available at the time the encounter document was signed.

System

FIG. 1 is a diagram illustrating an example system 100 for documenting an encounter, according to an embodiment. System 100 includes a computing device 110 and an EHR system 130 connected by one or more networks 120, such as the Internet. EHR system 130 includes at least EHR server 134 and medical records database 138.

Computing device 110 may be any type of computing device, such as, for example and without limitation, a personal computer, a mobile phone, a tablet, a personal digital assistant (PDA), a workstation, an embedded system, a game console, a television, a set top box, or the like. Computing device 110 may, for example, include a web browser application that enables a user to log into an EHR system. The web browser application responds to user input, such as a user selection on an EHR interface, by sending a hypertext transfer protocol (HTTP) request to EHR server 134 in EHR system 130 via network 120. In another example, the user may interface with computing device 110 through a native application instead of a web browser, such that the native application communicates with EHR system 130.

EHR system 130 includes at least EHR server 134 coupled to medical records database 138. In an embodiment, EHR server 134 is coupled to medical records database 138 via a network, such as the Internet or a local area network (LAN). In another embodiment, EHR server 134 and medical records database 138 are implemented on the same computing system and/or device. EHR server 134 includes multiple layers, including an application logic layer, as described in U.S. patent application Ser. No. 14/455,091, filed on Aug. 8, 2014, entitled *Electronic Health Records Data Management Systems and Methods*, which is incorporated herein by reference in its entirety. In addition, an example of establishing communications between a computing device and an EHR system is described in U.S. patent application Ser. No. 14/318,492, filed on Jun. 27, 2014, entitled *Medical Professional Application Integration into Electronic Health Record System*, which is incorporated herein by reference in its entirety.

EHR server 134 may be implemented on one or more computing devices having server capabilities. Such a computing device may include, but is not limited to, a device having a processor and memory, including a non-transitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

In embodiments, EHR server 134 may output data to be displayed as a user interface on computing device 110. The user may make a selection and the user interface may be updated to present the user's selection, for example using callbacks to EHR server 134, as would be understood by one skilled in the art.

Medical records database 138 may be any type of structured data store, including a relational database, that stores a plurality of different types of patient medical data records. Each patient medical data record includes one or more categories of data and may reference additional categories. For example, a data record representing a laboratory result may contain data about the actual test results, and contain references to data about the specified patient and the practice that requested the laboratory test. Such references may be, for example, pointers to the referenced data in other databases, as described in U.S. patent application Ser. No. 14/455,091, incorporated by reference above.

Method

Figure 2:
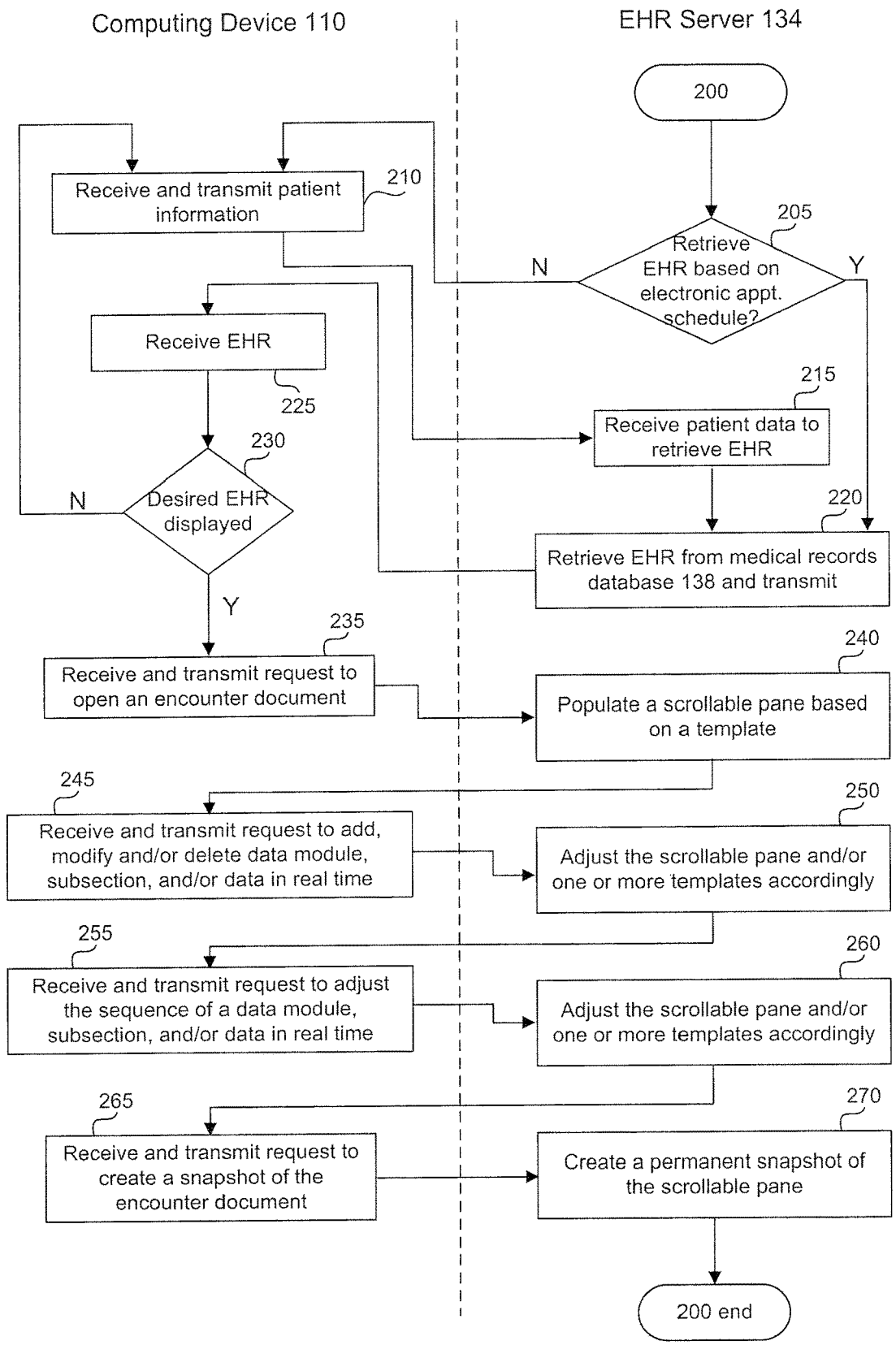
FIG. 2 is a flowchart illustrating an example method for documenting an encounter, according to an embodiment.

FIG. 2 is a flowchart illustrating an example method 200 for documenting an encounter, according to an embodiment. For ease of discussion and not limitation, method 200 will be described herein with reference to elements from FIG. 1 and FIGS. 3-7. Method 200 begins at step 205.

At step 205, a determination is made whether an EHR is to be retrieved based on a user's electronic schedule. When the EHR is not to be retrieved based on the user's electronic schedule, method 200 proceeds to step 210. When the EHR is to be retrieved based on the user's electronic appointment schedule (e.g., based on the patients scheduled for the current time and date), method 200 proceeds to step 220.

At step 210, computing device 110 receives patient information from the user. In an embodiment, the user provides patient data including but not limited to one or more of the following: a last name, a first name, a birth date, a social security number, an insurance policy number, an identifier that uniquely identifies the patient's EHR, and the like. Computing device 110 transmits the patient data to EHR server 134.

At step 215, EHR server 134 receives the patient data or the request identifying the desired EHR.

At step 220, EHR server 134 retrieves the patient's EHR from medical records database 138 and transmits the patient's EHR to computing device 110. The EHR may be formatted as a hypertext markup language (HTML) file, and may be transmitted to computing device 110 using web protocols such as HTTP to be displayed using a conventional web browser. Other protocols and devices may be used instead to output the EHR to a display on computing device 110.

If a group of EHRs are identified, EHR server 134 transmits the group of EHRs to computing device 110. A group of EHRs may be identified, for example, based on the user's electronic appointment schedule (e.g., patients scheduled for the current date) or based on patient data received from the user (e.g., patients with the same birth date).

At step 225, computing device 110 receives the patient's EHR or a group of EHRs.

At step 230, a determination is made whether the desired EHR is displayed. When the desired EHR is not displayed, method 200 proceeds to step 210 as described above. When the desired EHR is displayed (e.g., if the desired EHR is presented in a group of EHRs, the user may select the desired EHR and) method 200 proceeds to step 235.

At step 235, computing device 110 receives an indication from the user to open an encounter document. The encounter document may be a new encounter document or an encounter document that was previously opened but not yet signed. When the encounter document is opened, the user can record notes about the patient encounter. For example, the user may choose a selectable item associated with an encounter type from the EHR interface presented on computing device 110. Example encounter types include but are not limited to: an office visit encounter, a hospital visit encounter, a telephone encounter, or an order encounter. Based on the user indication, computing device 110 transmits a request to open an encounter document to EHR server 134.

At step 240, EHR server 134 receives the request to open an encounter document, and retrieves one or more data modules to be serialized in a scrollable pane of the encounter document based on at least one template. In an embodiment, a template is based on the user's medical practice type, a user work flow, an encounter type, a medical condition, a patient age, a particular patient, or the like. For example, a template may be based on the user's type of practice or medical specialty, such as pediatrics, cardiology, obstetrics, family practice, or oncology. The data modules that each specialty uses may be generic to multiple practice types (e.g., vitals including patient's blood pressure and temperature) or specific to a practice type (e.g., a pediatrics practice may include growth chart details, whereas a cardiologist may not need or want that data to be included). Even within the same type of practice, a user may have a unique work flow, and one user may perform tasks in a different manner and/or a different sequence than another user. For example, a pediatrician may choose to review growth chart details first while another pediatrician may choose to review allergies first. Thus, the user's practice type and unique work flow affect the type and sequence of data modules included in the scrollable pane of the encounter document.

In an embodiment, a template is based on the selected encounter type, including but not limited to an office visit encounter, a hospital visit encounter, a telephone encounter, or an order encounter. For example, an office visit encounter document may include the following data modules serialized in the scrollable pane: allergies, medications, family health history, and vitals. But a telephone encounter where the user interacts with a patient over the telephone may not include the vitals data module if the user cannot measure and record vitals data (e.g., patient's blood pressure).

In another embodiment, a template is based on a medical condition, a patient age, or the like. For example, the user may include and/or arrange a different set of data modules for patients that have been diagnosed with a particular condition than for other patients. Examples include, but are not limited to, a pregnant patient, a diabetic patient, a patient with immune deficiency, a senior patient, and a newborn patient.

An encounter document can be populated by pulling data from one or more databases based on at least one of a template specific to a particular patient, a template that applies to all patients, a template that applies to a patients with a certain medical condition, or a combination of templates.

Thus, the templates are important so that the user does not have to manually enter relevant data. Rather, the encounter document is populated based on the template(s) so that the relevant information is collected in one place, a scrollable pane arranged according to the user's work preferences (e.g., work flow), and will be saved.

As an example, when the user selects an office visit encounter, EHR server 134 retrieves and transmits data modules to be displayed on computing device 110 as described in U.S. patent application Ser. No. 14/455,091, incorporated by reference above. FIG. 3 illustrates an example interface 300 showing an office visit encounter document, according to an embodiment. The document includes scrollable pane 310 and scroll bar item 320. Examples of the data modules in the scrollable pane include but are not limited to Encounter details 325, Chief complaint 330, Vitals 335, Problem list 340, Allergies 350, and Medications 360. A data module may include subsections of data. For example, the Allergies data module 350 includes Drug allergies subsection 353 that includes data 355 (e.g., Penicillin).

At step 245, the user may customize the encounter document and/or a template in real time by choosing selectable items on a user interface displayed on computing device 110. For example, the user may add, change, or delete data modules, subsections, and/or data in scrollable pane 310 in real time. Data not being customized remains present in scrollable pane 310. Computing device 110 receives an indication to add, modify, and/or delete a data module, subsection, and/or data from the user, and transmits a corresponding request to EHR server 134.

For example, during an office visit encounter the user may learn about a patient's recent allergic reaction to a medicine, and update the patient's office visit encounter document accordingly. FIG. 4 illustrates an example interface 400 showing data being added to a subsection, according to an embodiment. The user selects Record an allergy item 410, and Record allergy details pane 420 is presented on scrollable pane 450. The user selects Drug item 430 to add the medicine to Drug allergies subsection 415 of Allergies data module 405. The user enters the name of the medicine in search box 440 of Record allergy details pane 420. In an embodiment, the user enters other data including but not limited to: a severity level, the patient's reaction to the allergen, the onset of the reaction, and comments. While the user adds data (e.g., the medicine) to Drug allergies subsection 415, other data modules such as Medications 460 and Family health history 470, as well as associated subsections and data, remain present (e.g., visible) in the scrollable pane.

In an embodiment, the user minimizes and maximizes Record allergy details pane 420 to allow for flexibility in viewing the scrollable pane. For example, a user may select a minimize icon (e.g., a minus sign) on the Record allergy details pane 420 as shown in FIG. 4 to minimize and/or hide the pane from view. The minimized details Record allergy details pane 420 allows for visibility of other data in the scrollable pane of the encounter document that may be blocked when Record allergy details pane 420 is expanded. The user selects a maximizing icon (e.g., a plus sign) to expand the data in the Record allergy details pane 420 by rolling subsections and data down. In an embodiment, Record allergy details pane 420 may be scrollable.

Figure 5:
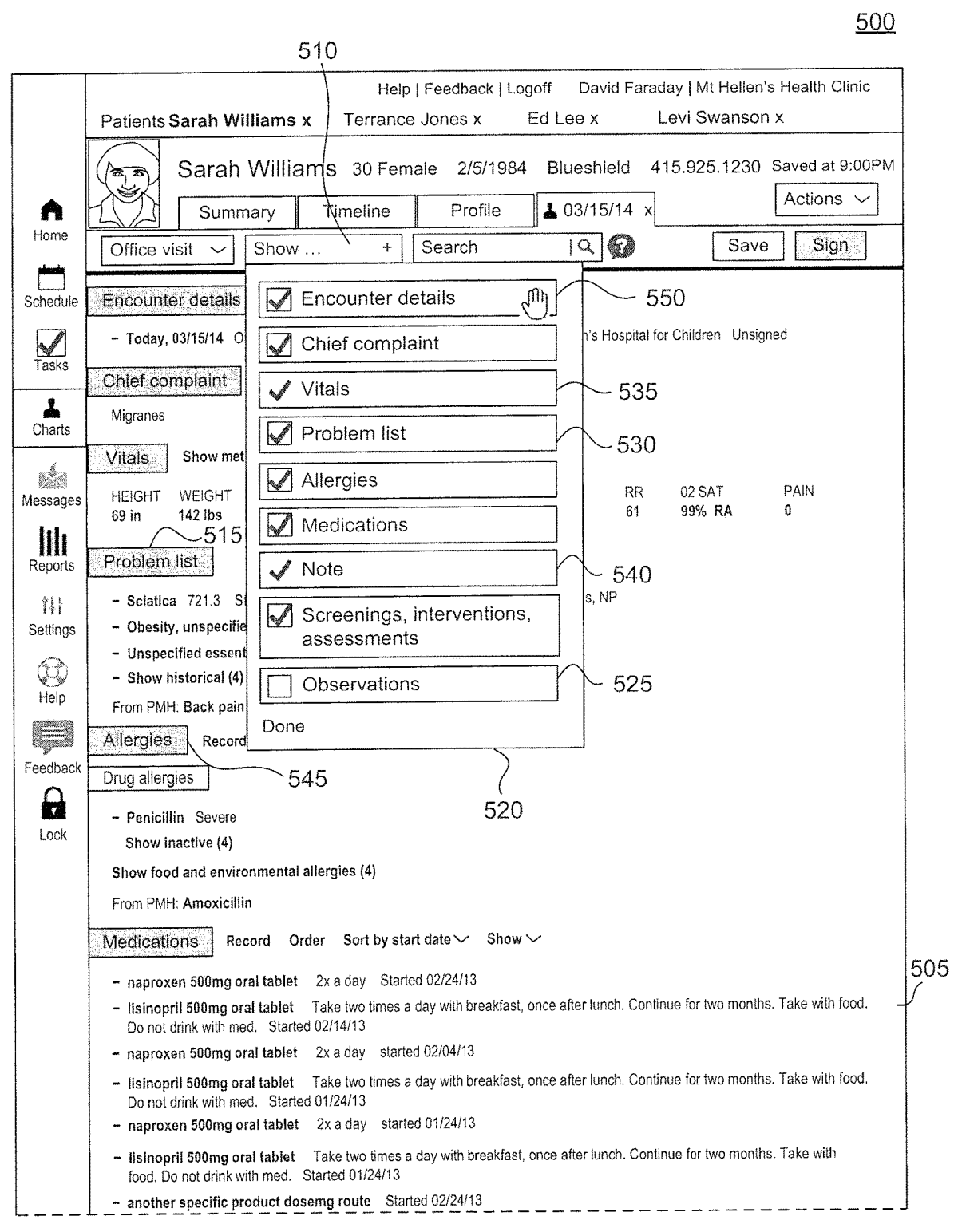

In an embodiment, a user adds a new data module as a section header. FIG. 5 illustrates an example interface 500 showing data module choices, according to an embodiment. For example, by selecting Show item 510, details pane 520 is presented on scrollable pane 505. Details pane 520 displays a plurality of data modules available to the user. Data modules not currently in the scrollable pane may be presented differently from data modules that are currently in scrollable pane 505. For example, Observations item 525 is not selected (e.g., not checked) indicating that it is not currently in scrollable pane 505.

Details pane 520 indicates whether the user may add or remove a data module to or from scrollable pane 505. For example, Problem list item 530 may be unselected (e.g., unchecked), resulting in Problem list data module 515 being removed from scrollable pane 505. Also, Observations data module 525 may be selected (e.g., checked), resulting in an Observations data module and associated data becoming present on scrollable pane 505. In another example, some data modules deemed essential for office visit encounters may not be adjusted (e.g., unselected) such as Vitals item 535 and Note item 540.

At step 250, EHR server 134 receives the request to add, modify, and/or delete a data module, subsection, and/or data from computing device 110 as illustrated in FIG. 5. EHR server 134 dynamically updates the contents of scrollable pane 505 in the patient's office visit encounter document of EHR interface 500 accordingly. During the update the contents not being adjusted, data modules (e.g., Allergies data module 545), subsections, and data, remain present in scrollable pane 505. The user may scroll up and down to view the contents of scrollable pane 505 during the update. In addition, the user may choose to minimize or maximize details pane 520 in scrollable pane 505 during the update.

In an embodiment EHR server 134 modifies at least one of the following based on the adjustments made during an encounter: the current patient's unsigned encounter document; a template specific to the patient (e.g., the current patient's office visit encounter document template), a template that affects all the user's patients (e.g., a user's practice type template), a template that affects a type of encounter document (e.g., an office visit encounter document template), a template associated with a patient's age (e.g., a template associated with senior patients), or a template associated with a medical condition, (e.g., a template associated with diabetes).

At step 255, computing device 110 receives a user indication to adjust the sequence of a data module, subsection, and/or data in the scrollable pane of the unsigned encounter document. The user makes the sequence adjustment in real time, during a patient encounter. For example, the user may move a data module to change the sequence of one or more data modules, and/or nest data modules hierarchically in a scrollable pane of an encounter document via an interface presented on computing device 110, prior to signing the encounter document. Based on the user indication, computing device 110 transmits a corresponding request to EHR server 134.

Figure 6:
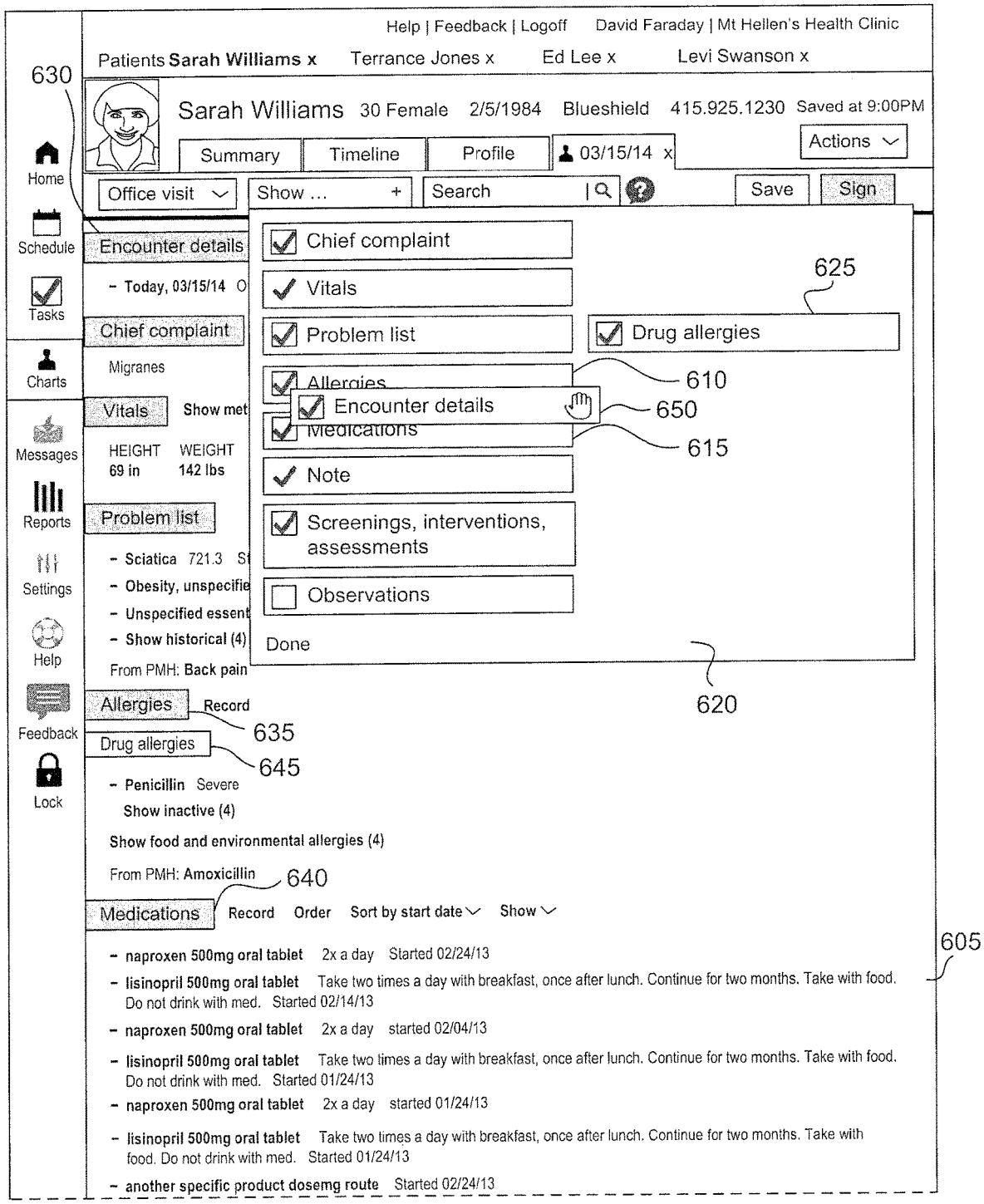
FIG. 6 illustrates an example interface showing moving, adjusting the sequencing, and hierarchical nesting among the plurality of modules of data, according to an embodiment.

FIG. 6 illustrates an example interface 600 showing moving, sequencing, and hierarchical nesting among the plurality of data modules, according to an embodiment. If for example, a user wants Encounter details data module 630 to appear on scrollable pane 605 between Allergies data module 635 and Medications data module 640, the user selects and moves Encounter details item 650 between Allergies item 610 and Medications item 615.

Alternatively, the user may hierarchically nest contents of scrollable pane 605. For example, if the user wants Encounter details data module 630 to be serialized and sequenced in the Drug allergies subsection 645 in a second-level nested hierarchy, the user selects, moves, and hovers Encounter details item 650 over Allergies item 610 to make Drug allergies subsection item 625 visible. The user then moves Encounter details icon 650 over Drug allergies item 625. Other hierarchy levels are also possible, as would be known to one skilled in the art.

At step 260, EHR server 134 receives the request from computing device 110 to adjust the sequence of a data module, subsection, and/or data in the scrollable pane of the unsigned encounter document, and dynamically adjusts the sequencing within the scrollable pane accordingly. During the adjustment, the remaining data modules, subsections, and data remain present in the scrollable pane.

In an embodiment, EHR server 134 modifies at least one of the following based on the sequence adjustments made during an encounter: the current patient's unsigned encounter document; a template specific to the patient, a template that affects all the user's patients, a template that affects a type of encounter document, a template associated with a patient's age, or a template associated with a medical condition.

At step 265, computing device 110 receives an indication from the user to create a permanent snapshot of the encounter document. In an embodiment, a user selects the various data modules and information of scrollable pane 705 to be saved in the snapshot. In an embodiment, the user chooses a selectable item such as a "Sign" button to electronically sign the encounter document. Once signed, the contents of the scrollable pane in the encounter document are viewable, but not changeable. FIG. 7 illustrates an example interface 700 that allows for the creation of a snapshot, according to an embodiment. For example, the user selects sign item 710 that causes a snapshot of scrollable pane 705 to be captured and documented. Based on the user indication, computing device 110 transmits a corresponding request to create a permanent snapshot to EHR server 134.

At step 270, EHR server 134 receives the indication from computing device 110, creates a snapshot of scrollable pane 705 of the encounter document, stores the snapshot without any protected health information (e.g., patent-identifiable data), and stores a link of the permanent snapshot with the user and/or the patient's EHR. For example, the data to be saved in the snapshot undergoes a de-identification process so that the snapshot data is stored without patient identification. However, the link or relationship between the permanent snapshot data, the user, and/or the patient's EHR is stored so that the user may retrieve the permanent snapshot data. Thus, the user may return to the snapshot of the encounter document to view the data available at the time the encounter document was signed. Method 200 ends.

Computing Device

Figure 8:
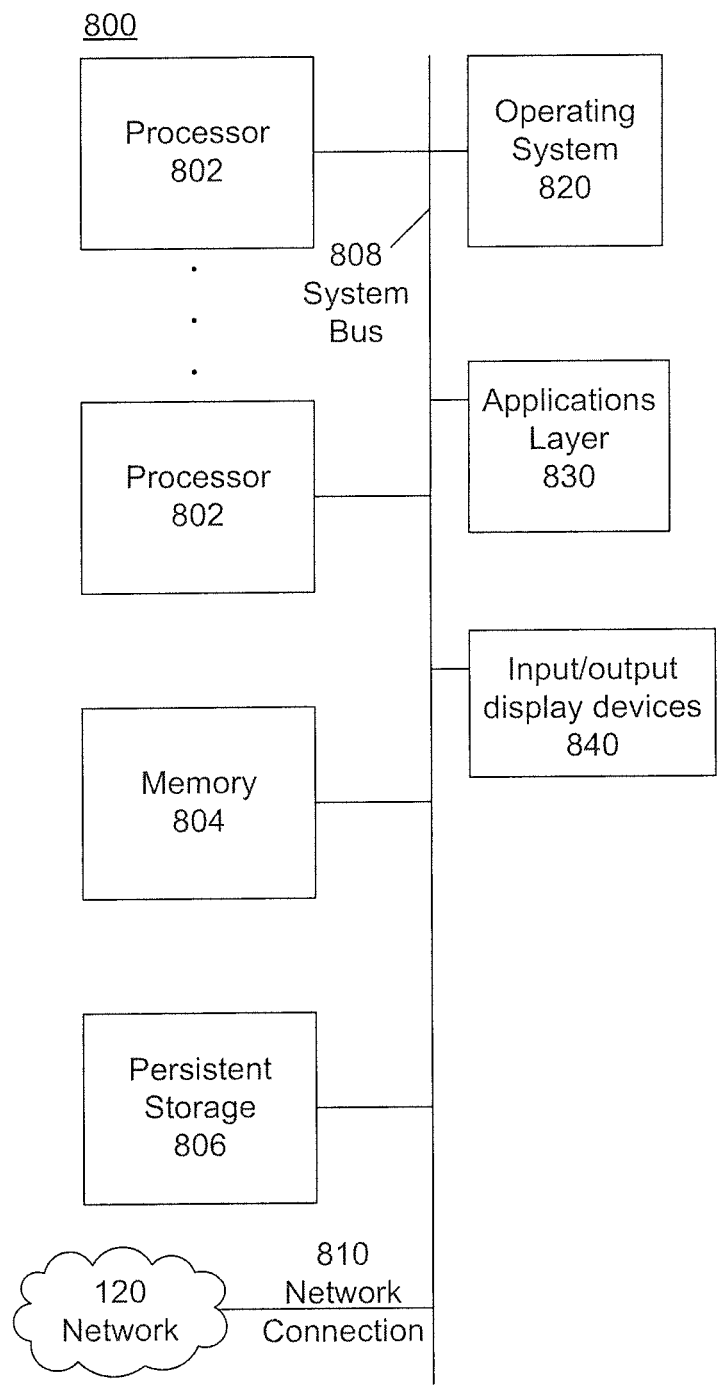
FIG. 8 is a diagram illustrating an example computing device, according to an embodiment.

An example computing device is illustrated in FIG. 8. FIG. 8 is a diagram illustrating a computing device 800 that accesses a network 120 over a network connection 810 that provides computing device 800 with telecommunications capabilities. Computing device 800 uses an operating system 820 as software that manages hardware resources and coordinates the interface between hardware and software.

In an embodiment, computing device 800 contains a combination of hardware, software, and firmware constituent parts that allow it to run an applications layer 830. Computing device 800, in embodiments, may be organized around a system bus 808, but any type of infrastructure that allows the hardware infrastructure elements of computing device 800 to communicate with and interact with each other may also be used.

Processing tasks in the embodiment of FIG. 8 are carried out by one or more processors 802. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 802 may be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

To manipulate data in accordance with embodiments describe herein, processors 802 access a memory 804 via system bus 808. Memory 804 is non-transitory memory, such as random access memory (RAM). Memory 804 may include one or more levels of cache. Memory 804 has stored therein control logic (i.e., computer software) and/or data. For data that needs to be stored more permanently, processors 802 access persistent storage 806 via system bus 808. Persistent storage 806 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 802, memory 804, and persistent storage 806 cooperate with operating system 820 to provide basic functionality for computing device 800. Operating system 820 provides support functionality for applications layer 830. Applications layer 830 may perform functions described in FIG. 2 when computing device 800 is used as EHR server 134 or computing device 110.

Network connection 810 enables computer device 800 to communicate and interact with any combination of remote devices, remote networks, remote entities, etc. For example, network connection 810 may allow computer device 800 to communicate with remote devices over network 120, which may be a wired and/or wireless network, and which may include any combination of LANs, WANs, the Internet, etc. Control logic and/or data may be transmitted to and from computer device 800 via network connection 810.

It should be noted that computer-readable medium embodiments may include any physical medium which is capable of encoding instructions that may subsequently by used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A server computing device comprising:
a processor; and
memory that has a server electronic health record application (EHR) loaded therein, wherein the server EHR, when executed by the processor, causes the processor to perform acts comprising:
responsive to receiving a request to transmit an encounter document pertaining to a patient, transmitting the encounter document to a client EHR executing on a client computing device in network communication with the server computing device, wherein the encounter document is based upon an encounter document template, and further wherein the encounter document, when displayed on a graphical user interface (GUI) of the client EHR, comprises a data field populated with patient data included in an electronic health record of the patient maintained by the server EHR;
responsive to receiving an indication that a modification has been made to the encounter document at the client computing device, updating the encounter document template based upon the modification;
subsequent to receiving a snapshot of the modified encounter document, the snapshot of the modified encounter document captured at the client computing device, wherein the snapshot comprises the patient data included in the modified encounter document, storing the snapshot of the modified encounter document in a database maintained by the server EHR, and wherein the contents of the snapshot are not changeable;
subsequent to storing the snapshot of the modified encounter document, receiving a request to transmit the snapshot of the modified encounter document to the client computing device; and
transmitting the snapshot of the modified encounter document to the client computing device for display on the GUI.

2. The server computing device of claim 1, wherein the encounter document includes a plurality of sections, each of the sections pertaining to a different type of patient data, and wherein a first section in the plurality of sections includes the data field, wherein the modification comprises replacing a second section in the plurality of sections with a third section, wherein the second section is representative of a second type of patient data and the third section is representative of a third type of patient data.

3. The server computing device of claim 2, wherein updating the encounter document template comprises updating the encounter document template to include the third section.

4. The server computing device of claim 1, the acts further comprising:

generating a de-identified copy of the modified encounter document based upon the snapshot of the modified encounter document received from the client computing device; and storing the snapshot of the de-identified copy of the modified encounter document in a database maintained by the server EHR.

5. The server computing device of claim 4, the acts further comprising:

storing a link to the de-identified copy of the modified encounter document in the database maintained by the server EHR as part of the electronic health record of the patient.

6. The server computing device of claim 1, wherein transmitting the encounter document comprises selecting an encounter document template, wherein the encounter document template of the patient is selected based on at least one of:

an encounter type,
a medical condition of the patient, or
an age of the patient.

7. The server computing device of claim 6, wherein the encounter type comprises at least one of:

an office visit encounter,
a hospital visit encounter,
a telephone encounter, or
an order encounter.

8. A method performed by a server computing device, wherein at least one processor of the server computing device executes a server electronic health records (EHR) application, the method comprising:

responsive to receiving a request to transmit an encounter document pertaining to a patient, transmitting the encounter document to a client EHR executing on a client computing device in network communication with the server computing device, wherein the encounter document is based upon an encounter document template, and further wherein the encounter document, when displayed on a graphical user interface (GUI) of the client EHR, comprises a data field populated with patient data included in an electronic health record of the patient maintained by the server EHR;

responsive to receiving an indication that a modification has been made to the encounter document at the client computing device, updating the encounter document template based upon the modification;

subsequent to receiving a snapshot of the modified encounter document, the snapshot of the modified encounter document captured at the client computing device, wherein the snapshot comprises the patient data included in the modified encounter document, storing the snapshot of the modified encounter document in a database maintained by the server EHR, and wherein the contents of the snapshot are not changeable;

subsequent to storing the snapshot of the modified encounter document, receiving a request to transmit the snapshot of the modified encounter document to the client computing device; and transmitting the snapshot of the modified encounter document to the client computing device for display on the GUI.

9. The method of claim 8, wherein the encounter document includes a plurality of sections, each of the sections pertaining to a different type of patient data, and wherein a first section in the plurality of sections includes the data field, wherein the modification comprises replacing a second section in the plurality of sections with a third section, wherein the second section is representative of a second type of patient data and the third section is representative of a third type of patient data, wherein updating the encounter document template comprises updating the encounter document template to include the third section.

10. The method of claim 8, the method further comprising:

generating a de-identified copy of the modified encounter document based upon the snapshot of the modified encounter document received from the client computing device; and storing the snapshot of the de-identified copy of the modified encounter document in a database maintained by the server EHR.

11. The method of claim 10, wherein the snapshot of the de-identified copy of the modified encounter document is linked to a user profile.

12. The method of claim 10, the method further comprising:

storing a link to the de-identified copy of the modified encounter document in the database maintained by the server EHR as part of the electronic health record of the patient.

13. The method of claim 8, wherein transmitting the encounter document comprises selecting an encounter document template, wherein the encounter document template of the patient is selected based on at least one of:

an encounter type,
a medical condition of the patient, or
an age of the patient.

14. The method of claim 13, wherein the encounter type comprises at least one of:

an office visit encounter,
a hospital visit encounter,
a telephone encounter, or
an order encounter.

15. A computer-readable storage medium comprising a server electronic health records application (server EHR) that, when executed by a processor of a server computing device, causes the processor to perform acts comprising:

responsive to receiving a request to transmit an encounter document pertaining to a patient, transmitting the encounter document to a client EHR executing on a client computing device in network communication with the server computing device, wherein the encounter document is based upon an encounter document template, and further wherein the encounter document, when displayed on a graphical user interface (GUI) of the client EHR, comprises a data field populated with patient data included in an electronic health record of the patient maintained by the server EHR;

responsive to receiving an indication that a modification has been made to the encounter document at the client computing device, updating the encounter document template based upon the modification;

subsequent to receiving a snapshot of the modified encounter document, the snapshot of the modified encounter document captured at the client computing device, wherein the snapshot comprises the patient data included in the modified encounter document, storing the snapshot of the modified encounter document in a database maintained by the server EHR, and wherein the contents of the snapshot are not changeable;

subsequent to storing the snapshot of the modified encounter document, receiving a request to transmit the snapshot of the modified encounter document to the client computing device; and transmitting the snapshot of the modified encounter document to the client computing device for display on the GUI.

16. The computer-readable storage medium of claim 15, wherein the encounter document includes a plurality of sections, each of the sections pertaining to a different type of patient data, and wherein a first section in the plurality of sections includes the data field, wherein the modification comprises replacing a second section in the plurality of sections with a third section, wherein the second section is representative of a second type of patient data and the third section is representative of a third type of patient data.

17. The computer-readable storage medium of claim 16, wherein updating the encounter document template comprises updating the encounter document template to include the third section in lieu of the second section.

18. The computer-readable storage medium of claim 15, the acts further comprising:

generating a de-identified copy of the modified encounter document based upon the snapshot of the modified encounter document received from the client computing device; and storing the snapshot of the de-identified copy of the modified encounter document in a database maintained by the server EHR.

19. The computer-readable storage medium of claim 18, the acts further comprising:

storing a link to the de-identified copy of the modified encounter document in the database maintained by the server EHR, wherein the link, when selected, causes the identity of the patient to be displayed on the GUI of the client computing device.

20. The computer-readable storage medium of claim 19, wherein transmitting the encounter document comprises selecting an encounter document template, wherein the encounter document template of the patient is selected based on at least one of: an encounter type, a medical condition, or an age of the patient, and further wherein an encounter type comprises at least one of: an office visit encounter, a hospital visit encounter, a telephone encounter, or an order encounter.

* * * * *